United States Patent
Shimizu et al.

[11] Patent Number: 6,131,414
[45] Date of Patent: Oct. 17, 2000

[54] METHOD FOR MAKING A PREFORM FOR OPTICAL FIBERS BY DRAWING A MOTHER INGOT

[75] Inventors: Yoshiaki Shimizu; Tadakatsu Shimada; Hideo Hirasawa, all of Annaka, Japan

[73] Assignee: Shin-Etsu Chemical Co., Ltd., Tokyo, Japan

[21] Appl. No.: 09/075,877

[22] Filed: May 12, 1998

[30] Foreign Application Priority Data

May 13, 1997 [JP] Japan ................................. 9-121855

[51] Int. Cl.⁷ ................................................. G01N 23/00
[52] U.S. Cl. ................................ 65/378; 65/382; 65/385; 65/425; 65/429; 65/433
[58] Field of Search ........................ 65/378, 382, 385, 65/425, 429, 433, 435

[56] References Cited

U.S. PATENT DOCUMENTS

| | | |
|---|---|---|
| 4,227,806 | 10/1980 | Watkins . |
| 4,579,571 | 4/1986 | Hicks, Jr. . |
| 4,597,785 | 7/1986 | Karbassiyoon et al. .................. 65/382 |
| 4,726,677 | 2/1988 | Glantschnig et al. . |
| 4,797,143 | 1/1989 | Chida et al. ............................. 65/382 |
| 4,934,818 | 6/1990 | Glantschnig et al. . |
| 5,192,350 | 3/1993 | Le Sergent ............................. 65/382 |
| 5,656,056 | 8/1997 | Braglia et al ........................... 65/382 |

FOREIGN PATENT DOCUMENTS

| | | |
|---|---|---|
| 482348 | 4/1992 | European Pat. Off. ................ 65/382 |
| 3913907 | 10/1990 | Germany . |
| 60-260435 | 12/1985 | Japan ..................................... 65/378 |
| 62-212240 | 9/1987 | Japan . |
| 62-226831 | 10/1987 | Japan . |
| 63-139024 | 6/1988 | Japan . |
| 63-176324 | 7/1988 | Japan . |
| 2-212328 | 8/1990 | Japan . |

OTHER PUBLICATIONS

P. Valenta et al.: "Ein optisches Verfahren zur Prüfung von Glasfaser–Vorformen", Elektronik, vol. 31, No. 12, Jun. 1982, pp. 93–94, XP002073398, Munchen, DE.

*Primary Examiner*—Stanley S. Silverman
*Assistant Examiner*—Michael P. Colaianni
*Attorney, Agent, or Firm*—McDermott, Will & Emery

[57] ABSTRACT

A method for drawing a mother ingot into a preform for optical fibers comprises providing a mother ingot, subjecting the mother ingot to measurement of a distribution of refractive index along radial directions thereof to determine a ratio of a core diameter to a clad diameter, and comparing the thus determined ratio with a predetermined ratio between the core diameter and the ingot diameter which ensures intended optical transmission characteristics, under which if the determined ratio is insufficient for the intended light transmission characteristics, the mother ingot is further processed until the predetermined ratio is substantially attained, and the resultant ingot is drawn to a preform, or if the determined ratio is acceptable on comparison with the predetermined ratio, the mother ingot is finally drawn.

9 Claims, 6 Drawing Sheets

SECTION OF PREFORM
ALONG RADIAL DIRECTIONS

METHOD FOR MAKING A PREFORM FOR OPTICAL FIBERS BY DRAWING A MOTHER INGOT

BACKGROUND OF THE INVENTION

1. Field of the Invention

This invention relates to a method for drawing a mother ingot into a preform for optical fibers wherein when the mother ingot is drawn into preforms for optical fibers, a finishing step can be omitted or simplified.

2. Description of the Prior Art

Figure 5:
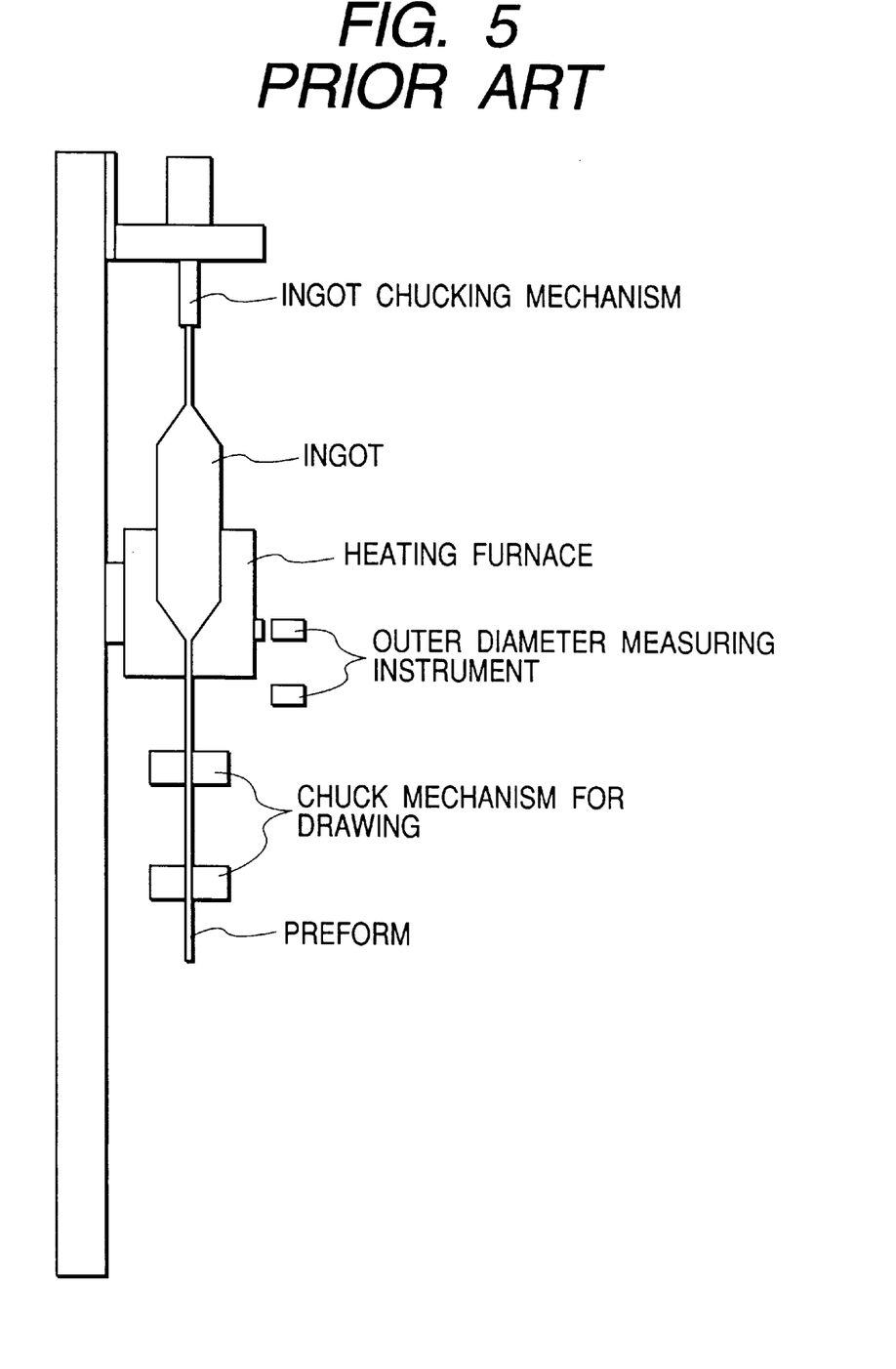
FIG. 5 is a schematic view illustrating a conventional drawing apparatus of a mother ingot.

For the fabrication of preforms for optical fibers form synthetic silica, a soot prepared, for example, by VAD is dehydrated and sintered to provide a mother ingot for preform. This ingot, usually having a diameter of 110 mm to 200 mm, is drawn to a diameter, which is larger by 3 to 5 mm than the diameter of the preform (e.g. 30 to 80 mm in diameter). In this drawing step, a glass-working lathe making use of an electric furnace or a flame burner has been usually employed. If the ingot has an outer diameter as small as 100 mm or below, it is possible to use a glass-working lathe for preliminary or primary drawing. For ingots having larger diameters, a flame burner is short of the quantity of heat, and thus, an electric furnace is ordinarily used. An electric furnace, which is employed for the drawing of an ingot, has such a structure that an ingot is fed form an upper portion of the electric furnace heated at about 2000° C., and a diameter-reduced preform is continuously taken off by means of rollers or drawing chucks from the lower portion of the furnace. This is particularly shown in FIG. 5, which illustrates the manner of the take-off of the preform by use of drawing chucks. In addition, outer diameter measuring instruments are provided to measure outer diameters at a neck portion of the ingot and also at a preform, respectively.

Figure 6:
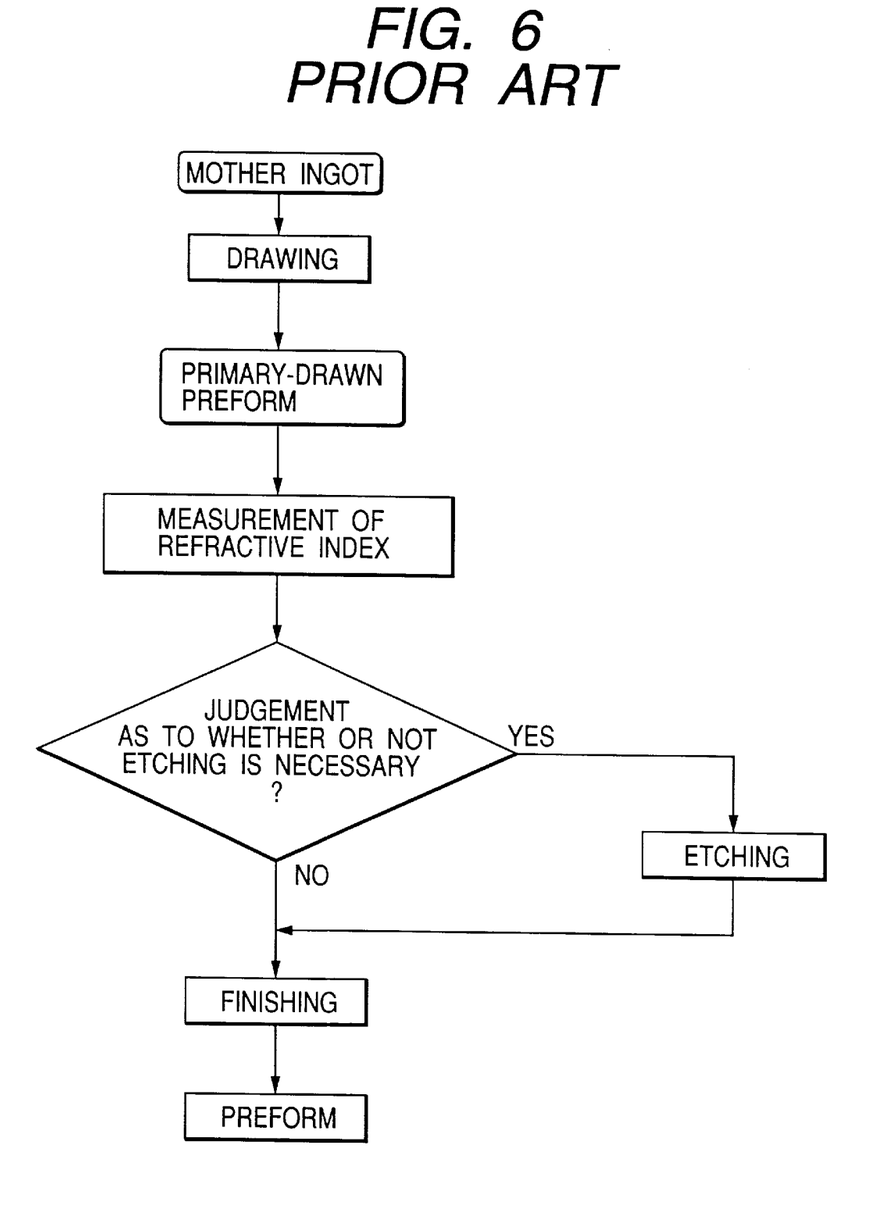
FIG. 6 is a flowchart showing a conventional procedure of fabricating a preform by drawing.

FIG. 6 is a flowchart showing a conventional process of drawing a preform. In the figure, a mother ingot is furnace-drawn such as in an electric furnace, and thus, is reduced in diameter to provide a primary-processed product, i.e. a preform. The outer diameter intended upon the drawing is set at a value greater by 5 to 10% than final intended value. The preform is subjected to measurement of a refracting index profile or distribution in radial directions. Based on the results of the measurement, optical transmission characteristics after drawing to a final optical fiber are estimated. The characteristics are decided depending on the refractive index profile or distribution of the preform, and especially, a ratio in diameter between the core portion and the clad portion (hereinafter referred to simply as "core-to-clad ratio") is an important parameter. In order to change the core-to-clad ratio, it is usually to etch the outer surface of the clad portion with hydrofluoric acid. By the etching, the core-to-clad ratio increases to an extent which is in coincidence with intended characteristics. More particularly, the characteristic properties of the ingot, which may vary from predetermined ones by many influences involved during the fabrication of a mother ingot, can be corrected according to subsequent processing steps. From the results of assumption of the characteristics, preforms whose characteristics should be corrected are etched for the correction. Those preforms, which need no correction, are fed to a next finishing step.

The finishing step is normally performed by means of a glass-working lathe. The primary drawing of the ingot in an electric furnace is carried out within a relatively short time of 1 to 2 hours. In this connection, however, the final drawing with a glass-working lathe takes about 1.5 hours per unit preform when a preform having a length of 1000 mm and a diameter of 43 mm is adjusted, for example, to a diameter of 40 mm. Thus, it takes an appreciably long time for processing preforms one by one, and it is desirable to reduce the degree or amount of the final drawing to an extent as small as possible.

In the above-stated conventional method, the index distribution is measured in the form of primary-processed preforms to assume optical transmission characteristics, and each preform is etched based on the results of the measurement as described hereinabove. This, in turn, requires that all preforms including ones, which do not need any adjustment of the characteristics after drawing, have to be drawn at a diameter, which is larger by 5 to 10% than an intended diameter. This means that preforms, which are not required of etching, have to be unavoidably subjected to final drawing.

SUMMARY OF THE INVENTION

It is accordingly an object of the invention to provide a method for drawing a mother ingot into preforms for optical fibers, which overcomes the drawbacks of the prior art method and wherein a finishing process, which undesirably takes a considerable time, can be omitted or simplified.

According to the invention, there is provided a method for drawing a mother ingot into a preform for optical fibers, which comprises providing a mother ingot, subjecting the mother ingot to measurement of distribution of refractive index along radial directions thereof to determine a ratio between the core diameter and the clad diameter, and comparing the thus determined ratio with a predetermined ratio between the core diameter and the ingot diameter which ensures intended optical transmission characteristics, under which if the determined ratio is insufficient for the intended optical transmission characteristics, the mother ingot is further processed until the predetermined ratio is substantially attained, and the resultant ingot is drawn to a preform, or if the determined ratio is acceptable on comparison with the predetermined ratio, the mother ingot is finally drawn.

In the manufacture of the perform for optical fibers by drawing a mother ingot according to the invention, the measurement of the profile of refractive index is made in the form of an ingot, and an intended outer diameter of a final preform is preset based on the results of the measurement. Thereafter, the mother ingot is drawn into a preform whose outer diameter substantially corresponds to the predetermined core-to-clad ratio. This enables one to omit or simplify a finishing process which required a long time.

DETAILED DESCRIPTION OF PREFERRED EMBODIMENTS

The drawing method of the invention is applicable to the manufacture of a preform which is particularly useful for making a single-mode optical fiber.

Figure 1:
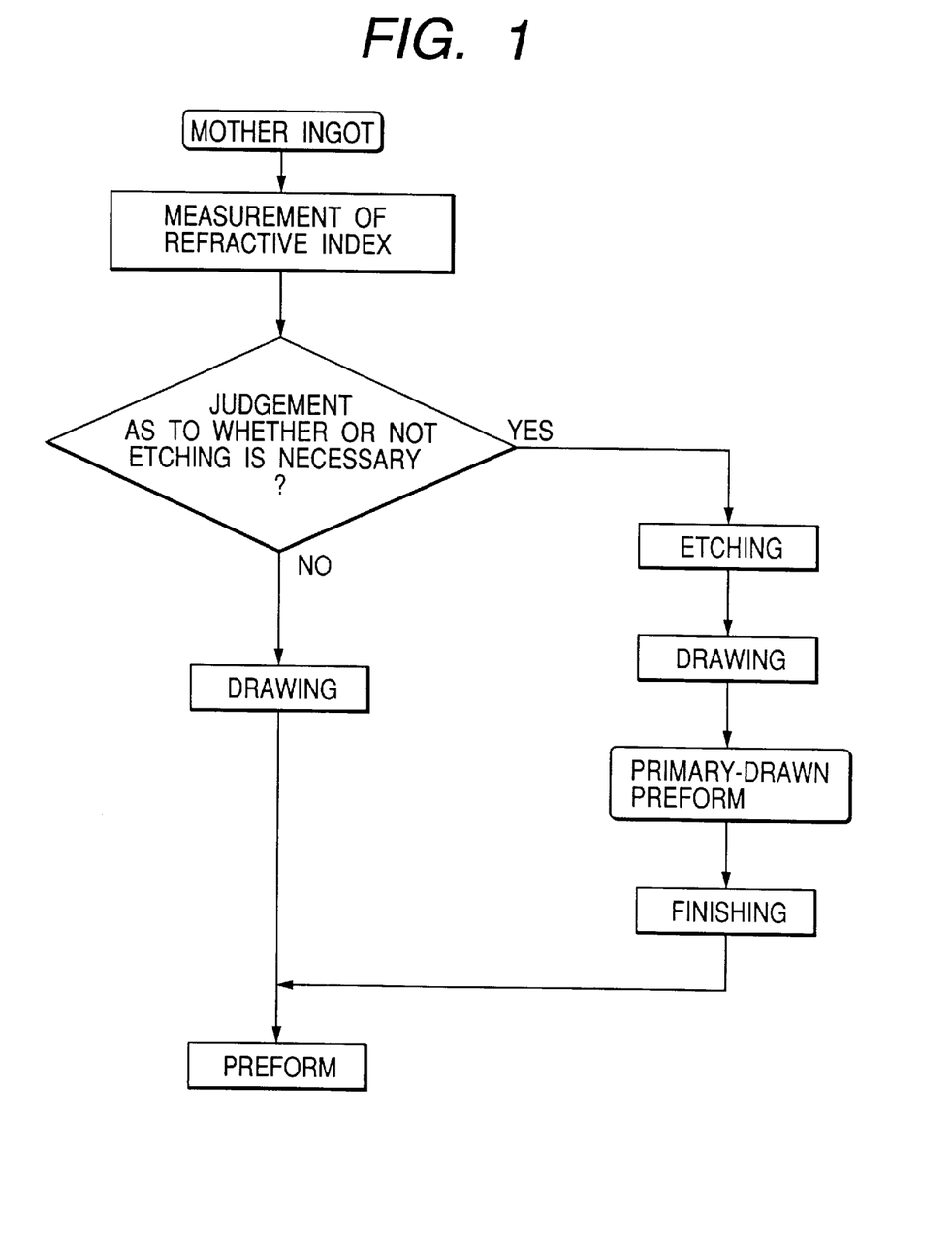
FIG. 1 is a flowchart showing a procedure of drawing a mother ingot according to one embodiment of the invention.
Figure 2:
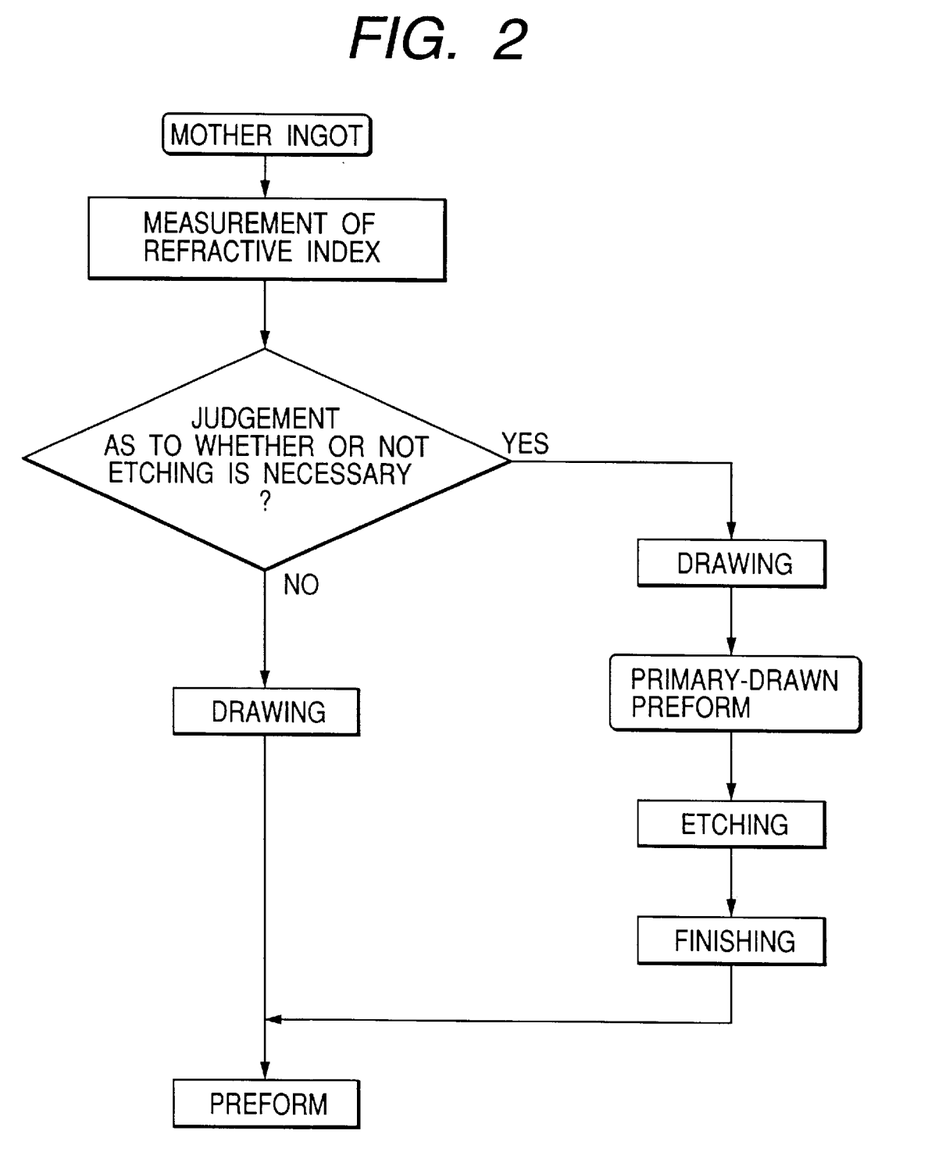
FIG. 2 is a flow chart showing a procedure of drawing a mother ingot into a preform according to another embodiment of the invention.

Reference is now made to the accompanying drawings and particularly, to FIGS. 1 and 2.

In the flowchart of FIG. 1, a mother ingot is provided. The mother ingot is made according to the VAD and/or OVD method using starting gases such as silicon tetrachloride and germanium tetrachloride. For instance, a target rod is suspended in a chamber having, at least, a burner for core, and is vertically drawn up while rotating, for example, at 30 r.p.m. In this condition, $SiCl_4$ along with an Ar carrier gas and $CeGl_4$ along with an Ar carrier gas are fed to the core burner together with hydrogen and oxygen gases, thereby forming a soot core. The core is dehydrated and consolidated, for example, at 1500° C. to form a transparent core. The transparent core is then subjected, for example to an OVD method wherein the target core is deposited with a soot clad by feeding $SiCl_4$ along with an Ar carrier gas and hydrogen and oxygen gases to a burner, followed by dehydration and consolidation in an electric furnace to obtain a transparent ingot. As a matter of course, the mother ingot may be made according to any of known techniques. In the practice of the invention, a soot for clad is deposited in an amount greater by 1 to 5% than an intended amount to bring a core-to-clad ratio closed to an intended value or to avoid discarding of the resultant ingot as unacceptable as will be discussed later.

In accordance with one embodiment of the invention, the ingot is initially subjected to the measurement of distribution of a refractive index along radial directions thereof. Based on the results of the measurement, i.e. the core-to-clad ratio, several optical transmission characteristics after fiber drawing can be estimated as will be described later. The mother ingot is etched or not etched depending on whether or not the core-to-clad ratio agrees to a predetermined core-to-clad ratio. If etching is judged as unnecessary, this ingot is directly drawn to a final preform having a final intended diameter. More particularly, if the measured core-to-clad ratio is within ±1% based on the predetermined ratio, the ingot is judged as acceptable. This ingot is directly passed to final drawing to obtain a final preform without performing any other steps.

On the contrary, if the measured core-to-clad ratio is within a range of smaller than −1% based on the predetermined ratio, etching is judged as necessary. This ingot is etched to an outer diameter, which meets the requirement for the predetermined core-to-clad ratio. The thus etched ingot is drawn to obtain a primary-drawn preform. The preform obtained in this way is subjected to a finishing step wherein the preform is, for example, flame polished by a usual manner to obtain a final preform.

Moreover, if the measured ratio is greater than 1% based on the predetermined ratio, such an ingot is not further processed but discarded. The predetermined core-to-clad ratio is preferably set at 1:15.5 to 1:12.

FIG. 2 shows another embodiment of the invention. In the figure, a mother ingot is subjected to measurement of an index distribution along radial directions, like FIG. 1. The optical transmission characteristics of the drawn optical fiber are estimated from the results of the measurement of the refractive index profile, from which the core-to-clad ratio is calculated. Since the core-to-clad ratio is in close relation with the optical transmission characteristics as will be described later, it is sufficient to judge an intended optical transmission characteristic or characteristics from the judgment of the ratio. More particularly, whether or not the ingot should be further processed depends on whether or not the measured core-to-clad ratio coincides with a predetermined core-to-clad ratio within the above-defined range of ±1% based on the predetermined ratio. If it is judged that etching is unnecessary, the ingot is drawn to an outer diameter which is in coincidence with a final intended diameter determined from the predetermined core-to-clad ratio, thereby obtaining a final preform. This is same as in the case of FIG. 1. On the contrary, when etching is judged as necessary, the ingot is first subjected to primary drawing, unlike FIG. 1. For the drawing, the outer diameter of the resultant primary-drawn preform is so set as to be greater by 5 to 15% than the intended outer diameter of a final preform. More particularly, the ingot is primarily drawn into a preform having an outer diameter, which corresponds to a final intended diameter+a depth of an outer surface portion to be etched, thereby obtaining a primary-drawn preform. This preform is etched to have the final intended diameter, followed by finishing such as by flame polishing to obtain a final perform by a usual manner. This is particularly described in examples appearing hereinafter.

Figure 3:
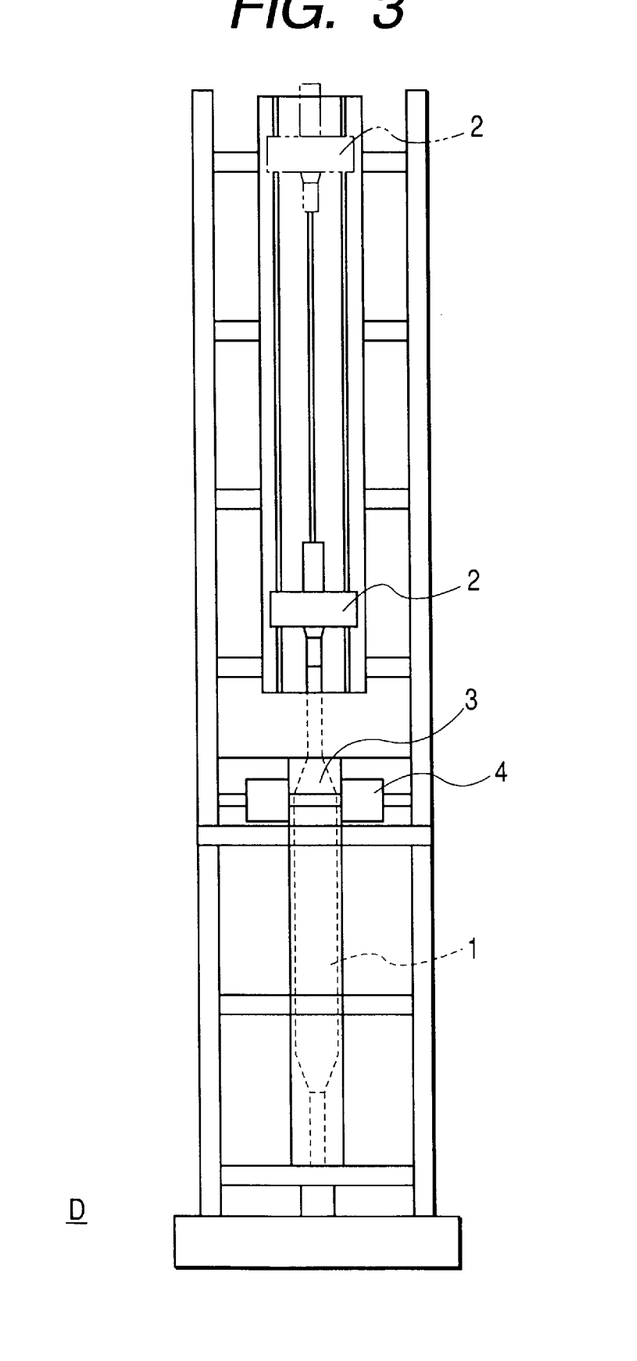
FIG. 3 is a schematic view showing a device of measuring a profile or distribution of refractive index of a mother ingot.

FIG. 3 schematically shows a device of measuring the index distribution of a mother ingot. In FIG. 3, a measuring device D includes a suspending mechanism 2 for suspending an ingot 1, a cell unit 3 capable of transmitting a beam when a laser beam is irradiated against the ingot 1, and an optical unit 4 capable of irradiating the ingot with a laster beam to measure an angle of refraction of a transmitted beam. The distribution of refractive index is obtained by a procedure wherein the ingot is set in the cell unit 3 filled with a matching oil, and is irradiated with a laser beam to measure an angle of refraction of a transmitted beam. The laser beam used for this purpose is one having an emission wavelength, for example, at 632.8 nm.

Figure 4:
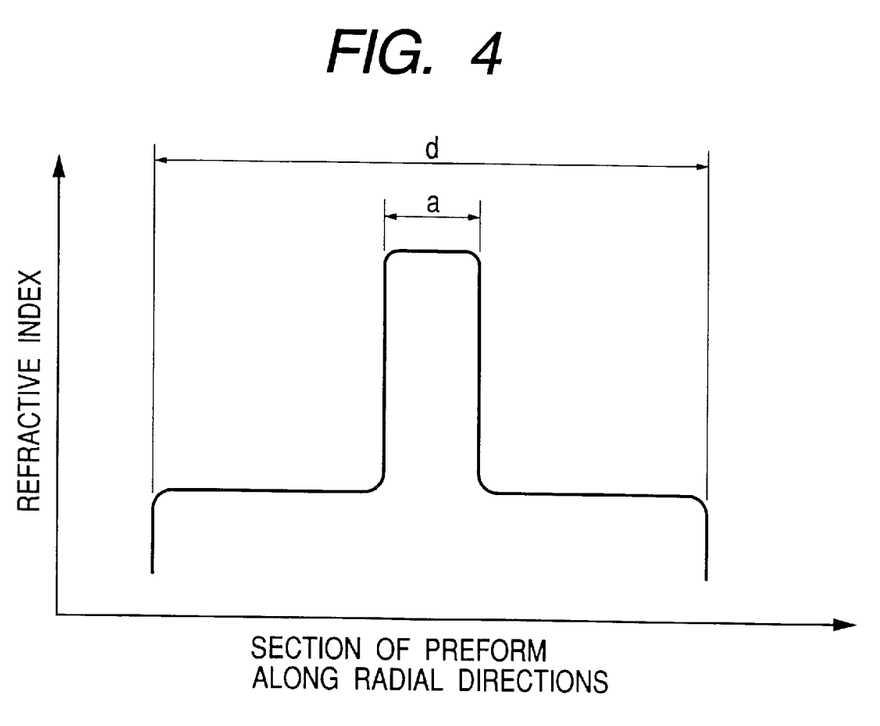
FIG. 4 is a view showing an index profile of a single-mode optical fiber preform along radial directions of the preform.

FIG. 4 schematically shows a profile of refractive index along radial directions of a single-mode optical fiber preform. From this profile, a ratio between core diameter (a) and clad diameter (d), i.e. a core-to-clad diameter ratio of a to d, is calculated. It will be noted that the term "core-to-clad ratio" used herein means a ratio of a to b shown in FIG. 4 throughout the specification.

Based on the core-to-clad ratio, optical transmission characteristics of an optical fiber obtained after fiber drawing, e.g. a mode field diameter (hereinafter abbreviated as MFD), a cut-off wavelength (hereinafter abbreviated as $\lambda c$), a zero dispersion wavelength ($\lambda_o$), a difference in refractive index between the core and the clad portions ($\lambda n$), and the shape of the core (e.g. eccentricity or non-circularity) can be readily estimated. Of these, the value or values of MFD and $\lambda c$ are estimated in most cases. In order to adjust the value of $\lambda c$, which requires a more severe control than MFD, the core-to-clad ratio corresponding to $\lambda c$ is used in practice. Anyway, the core-to-clad ratio depends proportionally on the values of these characteristics.

These characteristics are very liable to deviate form intended ones by various influences caused during the manufacture of mother ingots and should be corrected according to the procedures depicted in FIGS. 1 and 2.

The core-to-clad ratio of an ingot is determined from the measured index distribution, from which optical transmission characteristic or characteristics are estimated with respect to an optical fiber obtained after fiber drawing of the measured ingot. The comparison between the estimated characteristics and the intended characteristics enables one to determine wither or not the ingot it etched. As mentioned above, the mainly employed characteristic may be MFD and/or $\lambda c$. When the ingot or preform is etched, the core-to-clad ratio increases, thereby permitting both MFD and $\lambda c$ to increase.

The etching treatment may be those ordinarily used for this purpose. For instance, an ingot or preform is immersed in a vessel of circulating, for example, a hydrofluoric acid aqueous solution having a concentration, for example, of 50%. Depending on the difference between the estimated characteristics and the intended characteristics, the etching time is appropriately controlled. It will be noted that when using such an aqueous solution is mentioned above, an etching depth per unit hour is about 0.2 mm.

As having described hereinbefore, the etching treatment may be effected in the state of a mother ingot as shown in FIG. 1 or in the state of a preform after primary drawing as shown in FIG. 2.

The mother ingot usually has an outer diameter of 110 to 200 mm and a weight of 30 to 100 kg, so that a large-sized etching vessel undesirably becomes necessary. On comparison with the case using a primary-drawn preform as in FIG. 2, a greater etching depth is necessary, thus presenting the problem that it takes a longer etching time. In the present invention, it is preferred to deal with a mother ingot, which has a maximum value of an outer diameter at an effective portion of 100 mm or over.

On the other hand, where the preform obtained after primary drawing is etched as in the case of FIG. 2, its outer diameter ranges from 30 to 80 mm and a weight is as small as 3 to 10 kg, with ease in etching. The etching time can be shortened. However, preforms after the primary drawing become greater in number. This costs much time and labor on calculation as unit ingot. Thus, the etching treatments in the form of an ingot or preforms after primary drawing, respectively, have merits and demerits. It will be noted that etching in the form of preforms takes a long time of 5 to 30 hours, but labor is necessary only for setting and removing the preforms, so that an actual working time of workers is not so longer.

In FIG. 2, an ingot, which has to be etched, is primarily drawn to provide a thicker preform including a circumferential portion corresponding to an etching depth. The preform is etched so that its characteristics are at desired levels, followed by finishing with a glass-working lathe. At this stage, the outer diameter of the primary-drawn preform is one including the etching depth added to a final intended diameter. The diameter of the preform after the etching becomes substantially equal to the final one. Accordingly, the finishing with a glass-working lathe is substantially unnecessary. If unnecessary, the preform surface roughened with the etching is polished with a flame burner. That is, flame polishing, which does not take a long time, is sufficient for this purpose.

The surfaces of a preform, which is not etched, are substantially flat, and flame polishing is usually unnecessary. The preform, which has been etched, has relatively greater irregularities on the surface thereof, and should be flame polished by use of a glass-working lathe to flatten the surfaces in order to use it for fiber drawing. The time necessary for the flame polishing is about 40 minutes when using a preform having, for example, an outer diameter of 60 mm and a length of 1000 mm.

In case where a preform whose estimated characteristics are coincident with intended ones is not subjected to etching, a mother ingot is immediately finally drawn in an electric furnace, so that its final drawing with a glass-working lathe can be omitted. It will be noted that depending on the surface state after drawing, the drawn preform may be further processed or flame polished, if necessary.

The flame polishing, which is a finishing step using a glass-working lathe, can be completed within about 2 to 30 minutes irrespective of the diameter of a preform. The drawing time varies greatly depending on the difference in diameter between the preforms prior to and after drawing, and generally ranges from 60 to 120 minutes, which is longer than that required for the flame polishing. The processing with a glass-working lathe is partly automated, but labor is required in many cases. The shortage in time or omission of this step is very effective in simplification of a preform manufacturing process.

The invention is more particularly described by way of examples. Comparative examples are also shown.

EXAMPLE 1

Silicon tetrachloride and germanium tetrachloride used as starting gases for glass were subjected to a VAD method and an OVD method to form a soot as is well known in the art. The soot was dehydrated and consolidated to obtain a mother ingot for single-mode optical fiber having an outer diameter of 150 mm and a body length of 1200 mm. This ingot was subjected to measurement of a distribution of refractive index along radial directions thereof by use of a device of measuring the index distribution of the type shown in FIG. 3. The optical transmission characteristics of MFD, $\lambda c$, $\lambda_o$, $\Delta n$ and the like after drawing were estimated form the index distribution, revealing that a core-to-clad ratio in diameter was smaller by 2.5% than an intended ratio of 1:14. Accordingly, the ingot was etched. More particularly, the ingot was etched in a 50% hydrofluoric acid etchant while circulating the etchant for 10 hours. As a result, the surface layer of the ingot was removed in a thickness of 1.9 mm. Thereafter, the ingot was washed with water, followed by drawing in an electric furnace to obtain a preform having an outer diameter of 40 mm and an overall length of 17 m. The preform was cut into 17 pieces each having a length of 1 m. The thus drawn preforms had etching marks left on the surfaces thereof, and each preform was set in a glass-working lathe, and amounts of gases were set at 70 liters/minute for oxygen and 120 liters/minute for hydrogen. The preform was flame polished with an oxyhydrogen flame burner to make a flat surface. The time required for the flame polishing was 30 minutes per unit preform, with a length of time being 8.5 hours.

EXAMPLE 2

A mother ingot for single-mode optical fiber, which was made in the same manner as in Example 1 and which had an outer diameter of 150 mm and a body length of 1200 mm, was subjected to measurement of a distribution of refractive index, followed by estimation of optical transmission characteristics, from which a predetermined core-to-clad ratio was decided. More particularly, it was found that the core-to-clad ratio was smaller by 2.5% than an intended ratio of 1:14. The ingot was preliminarily drawn in an electric furnace to obtain 17 preforms each having an outer diameter of 41 mm, which consisted of an outer diameter of 40 mm of a preform used for fiber drawing and an etching depth of 1 mm, and having a length of 1 m. All the preforms were, respectively, etched on the surface thereof in a hydrofluoric acid etchant in the same manner as in Example 1to a thickness of 0.5 mm. Since the etching of 17 preforms was performed at one time, the time required for the etching was 2.5 hours. The thus etched preforms, respectively, had etching marks thereon, and subjected to flame polishing by use of a glass-working lathe to obtain performs used for fiber drawing. The time required for the flame polishing was 30 minutes per unit preform, and a length of the polishing time was 8.5 hours.

EXAMPLE 3

A mother ingot for single-mode optical fiber, which was made in the same manner as in Example 1 and which had an outer diameter of 200 mm and a body length of 1500 mm, was subjected to measurement of a distribution of refractive index. As a result, it was found that an estimated core-to-clad ratio in a diameter was in coincidence with an intended ratio. Accordingly, the ingot was drawn in an electric furnace to a final intended diameter of 60 mm and cut into 17 preform pieces having an outer diameter of 60 mm and a length of 1 m (with an overall length of 16.6 m). The preforms were not finished because they were not etched with flat surfaces.

COMPARATIVE EXAMPLE 1

A mother ingot for single-mode optical fiber, which was made in the same manner as in Example 1 and which had an outer diameter of 150 mm and a body length of 1200 mm, was preliminarily drawn in an electric furnace to a level of 43 mm relative to a final intended diameter of 40 mm, and cut into 17 primary-drawn preform pieces each having a length of 1 m. The respective preforms were subjected to measurement of a distribution of refractive index, revealing that it was necessary to abduct a core-to-clad ratio by 2.5%. Accordingly, the surfaces of each preform were etched by means of a 50% hydrofluoric acid etchant to a thickness of 0.5 mm to provide a preform having an outer diameter of 42 mm. The time required for the etching of all the preforms was found to be 2.5 hours. Thereafter, each preform was set in a glass-working lathe, and amounts of gases were to set that oxygen was at 70 liters/minute and hydrogen was at 120 liters/minute. Each preform was subjected to final drawing from 42 mm in outer diameter to 40 mm by means of an oxyhydrogen flame burner. The time required for this was found to be 1 hour per unit preform, with a length of time being 17 hours. The preform, which had been finish drawn by use of the glass-working lathe, was attached with fine silica particles and subjected to flame polishing on the surfaces thereof to obtain a clean preform. The time required for the final polishing was 0.5 hours per unit preform, with a length of polishing time being 8.5 hours.

COMPARATIVE EXAMPLE 2

A mother ingot for single-mode optical fiber, which was made in the same manner as in Example 1 and which had an outer diameter of 150 mm and a body length of 1200 mm, was primary-drawn in an electric furnace to a level of 43 mm relative to a final intended diameter of 40 mm, and cut into 17 primary-drawn preform pieces each having a length of 1 m. The respective preforms were subjected to measurement of a distribution of refractive index, revealing that is was unnecessary to adjust a core-to-clad ratio. Accordingly, each preform was set in a glass-working lathe and finally drawn by means of an oxyhydrogen flame burner until 43 mm in outer diameter was reduced to 40 mm.

The time required for the drawing was 1.5 hours per unit preform with a length of time being 25.5 hours. The preform obtained after the final drawing with the glass-working lathe had fine silica particles deposited on the surfaces thereof, so that it was flame polished on the surfaces thereof to obtain a clean preform. The time required for the flame polishing was 0.5 hours per unit preform, with a length of time being 8.5 hours.

As will be apparent form the foregoing, in the conventional case where an ingot is preliminarily drawn in an electric furnace and subjected to measurement of a distribution of refractive index in the form of a preform, and was etched or not etched depending on the results of the measurement, followed by final drawing with a glass-working lathe and flame polishing, only the finishing with the lathe needs 34 hours in total. In contrast, according to the invention, an ingot is subjected to measurement of a distribution of refractive index, drawn and/or etched depending on the results of the measurement, followed by flame polishing with a glass-working lathe on the surfaces thereof, the lathing time can be shortened to 8.5 hours.

If an ingot is not etched, the finishing with a glass-working lathe can be omitted.

Thus, according to the method of the invention an outer diameter of a perform after drawing in an electric furnace can be brought close to a final intended one. This enables one to omit final drawing with a glass-working lathe or to reduce the degree of the final drawing, resulting in a remarkable reduction of the finishing time.

What is claimed is:

1. A method for drawing a mother ingot into a preform for optical fibers, comprising the steps of:

providing a mother ingot and determining a radial refractive index distribution thereof;

determining, based on the measured refractive index distribution, a ratio of a core diameter to a clad diameter;

determining, based on the determined diameter ratio whether a predetermined diameter ratio requirement is met;

drawing the mother ingot to a final preform having a predetermined diameter in the event that the predetermined diameter ratio is met;

processing the mother ingot, in the event that the predetermined diameter ratio is not met, to reduce the outer diameter of the other ingot and adjust the diameter ratio to the predetermined diameter ratio; and drawing the etched mother ingot into a final preform having a predetermined diameter.

2. A method as set forth in claim 1, wherein the step of drawing is carried out in an electric furnace and wherein the drawing reduces the diameter of the mother ingot to the predetermined diameter.

3. A method as set forth in claim 1, wherein the mother ingot, prior to drawing to form the final preform, has a maximum outer diameter of at least 100 mm.

4. A method as set forth in claim 1, wherein, in the event that the predetermined diameter ratio is not met, the mother ingot is processed by etching either prior to, or after primary drawing.

5. A method as set forth in claim 4, further comprising cutting the etched ingot into preforms and finally finishing each of the preform to obtain final preforms for fiber drawing.

6. A method as set forth in claim 4, further comprising the step of cutting the etched mother ingot into preforms and finally finishing each of the preforms to obtain final preforms for fiber drawing.

7. A method as set forth in claim 4, wherein said mother ingot is primary-drawn, cut into preform pieces having an outer diameter sufficient for etching, etched to the predetermined diameter and finished to obtain final preforms suitable for fiber drawing.

8. A method as set forth in claim 1, wherein the predetermined ratio is in the range of 1:15.5–1:12 wherein predetermined optical transmission characteristics are provided.

9. A method as set forth in claim 1, wherein the determined core diameter/clad diameter ratio is within a range of ±1% of the predetermined ratio before drawing the mother ingot into the final preform is permitted.

* * * * *